United States Patent
Heeres et al.

[11] Patent Number: 5,929,075
[45] Date of Patent: *Jul. 27, 1999

[54] APOLIPOPROTEIN-B SYNTHESIS INHIBITORS

[75] Inventors: Jan Heeres, Vosselaar; Leo Jacobus Jozef Backx, Arendonk; Robert Jozef Maria Hendrickx, Beerse; Luc Alfons Leo Van der Eycken, Vosselaar; Didier Robert Guy Gabriël de Chaffoy de Courcelles, Beerse, all of Belgium

[73] Assignee: Janssen Pharmaceutica, N.V., Beerse, Belgium

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/817,247

[22] PCT Filed: Oct. 19, 1995

[86] PCT No.: PCT/EP95/04111
  § 371 Date: Apr. 9, 1997
  § 102(e) Date: Apr. 9, 1997

[87] PCT Pub. No.: WO96/13499
  PCT Pub. Date: May 9, 1996

Related U.S. Application Data

[63] Continuation-in-part of application No. 08/455,304, May 31, 1995, Pat. No. 5,521,186.

[30] Foreign Application Priority Data

Oct. 27, 1994 [EP] European Pat. Off. ............ 94203120

[51] Int. Cl.⁶ ............... A61K 31/495; C07D 405/14; C07D 407/14
[52] U.S. Cl. ............ 514/252; 544/295; 544/364; 544/367; 544/369; 544/370; 544/298; 544/315; 544/319; 546/283.7; 548/127; 548/129; 548/182; 548/213; 548/225; 548/228; 548/229; 548/263.2; 548/144; 548/251; 548/255; 548/311.1
[58] Field of Search .................. 544/295, 366, 544/367, 369, 370, 298, 315, 319, 364; 548/127, 129, 182, 213, 225, 228, 229, 263.2, 144, 251, 255, 311.1; 514/252; 546/283.7

[56] References Cited

U.S. PATENT DOCUMENTS

| | | | |
|---|---|---|---|
| 4,267,179 | 5/1981 | Heeres et al. | 514/252 |
| 4,313,953 | 2/1982 | Heeres et al. | 424/269 |
| 4,931,444 | 6/1990 | Van Wauwe et al. | 514/252 |
| 5,521,186 | 5/1996 | Heeres et al. | 514/252 |

FOREIGN PATENT DOCUMENTS

| | | |
|---|---|---|
| 068544 | 1/1983 | European Pat. Off. . |
| 0118138 | 9/1984 | European Pat. Off. . |
| 0228125 | 7/1987 | European Pat. Off. . |
| 0283992 | 9/1988 | European Pat. Off. . |
| WO 94/20063 | 9/1994 | WIPO . |

OTHER PUBLICATIONS

Montserrat, *Chemical Abstracts*, vol. 106, No. 67321 (1987).

Chemical Abstract, vol. 106, No. 9, 67321f, Mar. 2, 1987, (Inke S.A.).

Montserrat CA, 106,67320e, Mar. 2, 1987 (Ineke S.A.).

*Primary Examiner*—Emily Bernhardt
*Attorney, Agent, or Firm*—Ellen Ciambrone Coletti

[57] ABSTRACT

The present invention provides novel compounds of formula

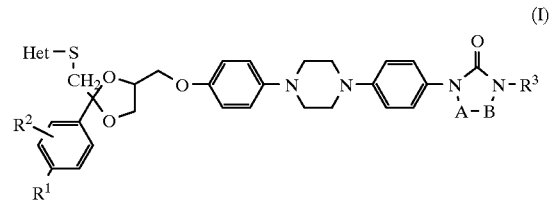

the N-oxides, the stereochemically isomeric forms thereof, and the pharmaceutically acceptable acid addition salts thereof, wherein A and B taken together form a bivalent radical of formula:

—N=CH— (a), —CH=N— (b), —CH$_2$—CH$_2$— (c), —CH=CH— (d), —C(=O)—CH$_2$— (e), —CH$_2$—C(=O)— (f); R$^1$ is hydrogen, C$_{1-6}$alkyl, or halo; R$^2$ is hydrogen or halo; R$^3$ is hydrogen; C$_{1-8}$alkyl; C$_{3-6}$cycloalkyl or C$_{1-8}$alkyl substituted with hydroxy, oxo, C$_{3-6}$cycloalkyl or aryl. Het is five- or six-membered optionally substituted heterocyclic ring. The use as a medicine, especially as a lipid lowering agent is disclosed as well as pharmaceutical compositions and processes for preparing compounds and compositions.

39 Claims, No Drawings

APOLIPOPROTEIN-B SYNTHESIS INHIBITORS

CROSS-REFERENCE TO RELATED APPLICATIONS

This application is the national stage of application No. PCT/EP 95/04111, filed on Oct. 19, 1995, which is a continuation-in-part of U.S. application Ser. No. 08/455,304, filed on May 31, 1995, now U.S. Pat. No. 5,521,186.

The present invention concerns novel compounds of formula (I), pharmaceutical compositions comprising said compounds, the preparation thereof as well as the use as a medicine in the treatment of hyperlipidemia.

The causal relationship between hypercholesterolemia, particularly that associated with increased plasma concentrations of low density lipoproteins (LDL) and very low density lipoprotein (VLDL) remnants, and premature atherosclerosis has gained widespread acceptance over the last few years. The consensus that treatment of hypercholesterolemia has therapeutic benefit has become widely accepted by both physicians and the public. A limited number of drugs are available for the treatment of hyperlipidemia. The primary agents used for the management of hyperlipidemia included bile acid sequestrants, fibrates, nicotinic acid and HMG Co A-reductase inhibitors. The inconvenience of administration and gastro-intestinal side-effects of available bile acid sequestrants make compliance a major problem. The fibrates have only limited usefulness in the treatment for certain types of hypercholesterolemia. Treatment with nicotinic acid encompasses side-effects and toxicity problems. The HMG Co A-reductase inhibitors already form a first line treatment of familiar hypercholesterolemia. However there still remains a need for new lipid lowering agents for that act preferably via other mechanisms than the above mentioned drugs.

EP-0,006,711-A, published on Sep. 9, 1980, discloses heterocyclic derivatives of (4-phenylpiperazin-1-yl-aryloxymethyl-1,3-dioxolan-2-yl)-methyl-1H-imidazoles and 1H-1,2,4-triazoles having antifungal properties. The presently claimed compounds differ therefrom by the presence of a sulfur atom adjacent to the Het-moiety and by their pharmacological profile, in particular their apolipoprotein B synthesis inhibiting activity. The present invention provides novel compounds of formula

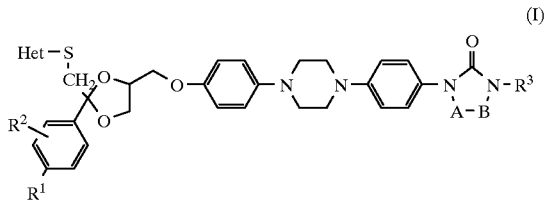

(I)

the N-oxides, the stereochemically isomeric forms thereof, and the pharmaceutically acceptable acid addition salts, wherein A and B taken together form a bivalent radical of formula:

—N=CH— (a),
—CH=N— (b),
—CH$_2$—CH$_2$— (c),
—CH=CH— (d),
—C(=O)—CH$_2$— (e),
—CH$_2$—C(=O)— (f), in the bivalent radicals of formula (a) and (b) the hydrogen atom may be replaced by $C_{1-6}$alkyl; in the bivalent radicals of formula (c), (d), (e), (f), one or two hydrogen atoms may be replaced by $C_{1-6}$alkyl;

$R^1$ is hydrogen, $C_{1-6}$alkyl or halo;

$R^2$ is hydrogen or halo;

$R^3$ is hydrogen; $C_{1-8}$alkyl; $C_{3-6}$cycloalkyl; or $C_{1-8}$alkyl substituted with hydroxy, oxo, $C_{3-6}$cycloalkyl or aryl;

Het is a heterocycle selected from the group consisting of pyridine; pyridine substituted with one or two substituents selected from $C_{1-6}$alkyl, hydroxy, $C_{1-6}$alkyloxy, trihalomethyl, amino, mono- or di($C_{1-6}$alkyl)amino or aryl; pyrimidine; pyrimidine substituted with one or two substituents selected from $C_{1-6}$alkyl, hydroxy, $C_{1-6}$alkyloxy, trihalomethyl, amino, mono- or di($C_{1-6}$alkyl)-amino or aryl; tetrazole; tetrazole substituted with $C_{1-6}$alkyl or aryl; triazole; triazole substituted with one or two substituents selected from $C_{1-6}$alkyl, hydroxy, $C_{1-6}$alkyloxy, trihalomethyl, amino, mono- or di($C_{1-6}$alkyl)-amino; thiadiazole; thiadiazole substituted with one or two substituents selected from $C_{1-6}$alkyl, hydroxy, $C_{1-6}$alkyloxy, trihalomethyl, amino, mono- or di($C_{1-6}$alkyl)amino; oxadiazole substituted with one or two substituents selected from $C_{1-6}$alkyl, hydroxy, $C_{1-6}$alkyloxy, trihalomethyl, amino, mono- or di($C_{1-6}$alkyl)amino; imidazole; imidazole substituted with one or two substituents selected from $C_{1-6}$alkyl, hydroxy, $C_{1-6}$alkyloxy, trihalomethyl, amino, mono- or di($C_{1-6}$alkyl)amino; thiazole; thiazole substituted with one or two substituents selected from $C_{1-6}$alkyl, hydroxy, $C_{1-6}$alkyloxy, trihalomethyl, amino, mono- or di($C_{1-6}$alkyl)amino; oxazole; oxazole substituted with one or two substituents selected from $C_{1-6}$alkyl, hydroxy, $C_{1-6}$alkyloxy, trihalomethyl, amino, mono- or di($C_{1-6}$alkyl)amino;

aryl is phenyl or phenyl substituted with $C_{1-6}$alkyl or halo.

The heterocyclic radical "Het" is bound to the sulfur atom via a carbon atom.

As used in the foregoing definitions halo is generic to fluoro, chloro, bromo and iodo; $C_{1-6}$alkyl defines straight and branched chain saturated hydrocarbon radicals having from 1 to 6 carbon atoms such as, for example, methyl, ethyl, propyl, butyl, pentyl, hexyl, 1-methylethyl, 2-methylpropyl and the like; $C_{1-8}$alkyl defines $C_{1-6}$alkyl and the higher homologues thereof containing 7 or 8 carbon atoms such as, for example, heptyl or octyl and the branched isomers thereof. $C_{3-6}$cycloalkyl defines saturated cyclic hydrocarbon radicals having from 3 to 6 carbon atoms, such as cyclopropyl, cyclobutyl, cyclopentyl, or cyclohexyl.

Het may in particular be a radical of formula

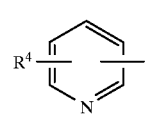

(a)

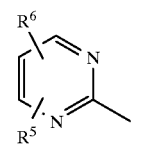

(b)

-continued

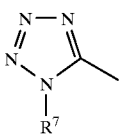 (c)

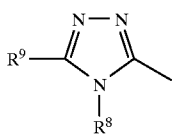 (d)

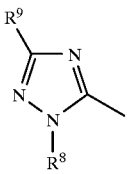 (e)

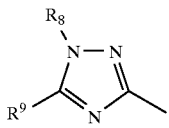 (f)

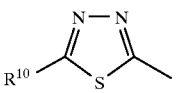 (g)

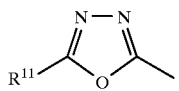 (h)

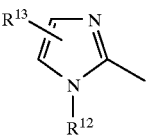 (i)

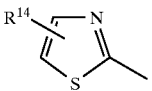 (j)

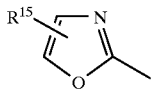 (k)

wherein:
$R^4$ is hydrogen or $C_{1-6}$alkyl;
$R^5$ and $R^6$ are hydrogen, $C_{1-6}$alkyl or amino;
$R^7$ is hydrogen or $C_{1-6}$alkyl;
each $R^8$ independently is hydrogen or $C_{1-6}$alkyl;
each $R^9$ independently is hydrogen, $C_{1-6}$alkyl, trifluoromethyl, amino or hydroxy;
$R^{10}$ and $R^{11}$ each independently are hydrogen or $C_{1-6}$alkyl;
$R^{13}$ is hydrogen or $C_{1-6}$alkyl;
$R^{14}$ is hydrogen, $C_{1-6}$alkyl or hydroxy;
$R^{15}$ is hydrogen or $C_{1-6}$alkyl.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric ; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like. Conversely the salt form can be converted by treatment with alkali into the free base form.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic saturated radicals may have either the cis- or trans-configuration. Stereochemically isomeric forms of the compounds of formula (I) are obviously intended to be embraced within the scope of this invention.

The N-oxide forms of the compounds of formula (I) are meant to comprise those compounds of formula (I) wherein one or several nitrogen atoms are oxidized to the so-called N-oxide, particularly those N-oxides wherein one or more of the piperazine-nitrogens are N-oxidized.

The substituents on the dioxolane moiety of the compounds of formula (I) may have the cis- or trans-configuration. The compounds of formula (I) having the cis-configuration are preferred.

The compounds of formula (I) wherein the stereogenic carbon in the 2-position of the dioxolane moiety has the S-configuration are also preferred.

The compounds of formula (I) may also exist in their tautomeric forms. For instance, heterocycles such as, for example, pyridine, pyrimidine, triazole, thiadiazole, oxadiazole, imidazole, thiazole and oxazole, which are substituted with hydroxy, amino or $C_{1-6}$alkylamino may exist in their tautomeric form. Such forms although not explicitly indicated in the above formula are intended to be included within the scope of the present invention.

A group of interesting compounds are those compounds of formula (I) wherein $R^1$ is chloro or fluoro, especially chloro.

Also a group of interesting compounds are those compounds of formula (I) wherein $R^1$ is $C_{1-6}$alkyl, especially methyl.

A further group of interesting compounds are those compounds of formula (I) wherein $R^2$ is hydrogen, chloro or fluoro, preferably hydrogen.

Another group of interesting compounds of formula (I) are those compounds wherein the bivalent radical —A—B— is —CH=CH—, —N=CH— or —CH=N—, especially —CH=N— or —N=CH—. In said bivalent radicals, the hydrogen atom may be replaced by $C_{1-6}$alkyl, especially methyl.

A particular group of compounds are those compounds of formula (I) and especially those interesting compounds wherein $R^3$ is $C_{1-8}$-alkyl or $C_{3-6}$-cycloalkyl, preferably butyl, pentyl or cyclopentyl.

A group of preferred compounds of formula (I) is formed by those compounds wherein Het is a triazole, substituted triazole, imidazole, substituted imidazole, thiazole, substituted thiazole.

More preferred compounds of formula (I) are those interesting or particular compounds wherein Het is 2-thiazolyl, 4-methyl-4H-1,2,4-triazol-3-yl, 4H-1,2,4-triazol-3-yl, 2-methyl-2H-1,2,4-triazol-3-yl or 2H-1,2,4-triazol-3-yl.

Most preferred compounds are cis-4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-2-(1-methylpropyl)-3H-1,2,4-triazol-3-one;

cis-2-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-4-(1-methylpropyl)-3H-1,2,4-triazol-3-one;

cis-2-[4-[4-[4-[[2-(4-fluorophenyl)-2-[[(4-methyl-4H-1,2,4-triazol-3-yl)thio]methyl]-1,3-dioxolan-4-yl]methoxy]phenyl]-1-piperazinyl]phenyl]-4-cyclopentyl-2,4-dihydro-3H-1,2,4-triazol-3-one;

cis-2-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-4-pentyl-3H-1,2,4-triazol-3-one;

cis-4-(1-ethylpropyl)-2-[4-[4-[4-[[2-(4-fluorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-3H-1,2,4-triazol-3-one; a pharmaceutically acceptable acid addition salt or a stereochemically isomeric form thereof.

The compounds of formula (I) may be prepared by O-alkylating a phenol of formula (II) with a 1,3-dioxolane derivative of formula (III), wherein W represents an appropriate leaving group such as halo, e.g. chloro or bromo, or a sulfonyloxy leaving group, e.g. 4-methylbenzenesulfonyloxy (tosylate) or methanesulfonyloxy (mesylate).

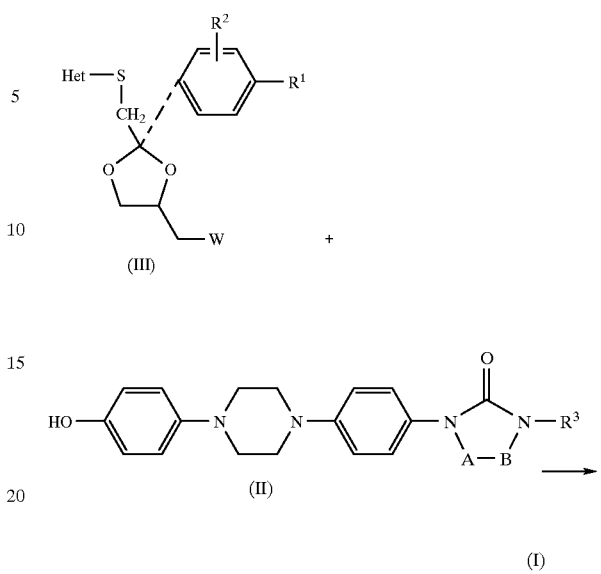

Said O-alkylation reaction can conveniently be conducted following art-known procedures, e.g. by stirring and heating the reactants in an appropriate solvent such as a dipolar aprotic solvent, e.g. N,N-dimethylformamide, N,N-dimethylacetamide, in the presence of a base such as, an alkali metal hydroxide or carbonate, e.g. sodium or potassium hydroxide, or sodium or potassium carbonate.

Intermediates of formula (II) may be prepared in similar ways as disclosed in EP-0,006,711, mentioned hereinabove. EP-0,331,232-A, published on Sep. 6, 1989 and WO 93/19061, published on Sep. 30, 1993, also disclose ways of preparing intermediates of formula (II).

The compounds of formula (I) may also be prepared by reacting an intermediate of formula (IV), wherein W is an appropriate leaving group as defined hereinabove with a heterocyclic derivative of formula (V).

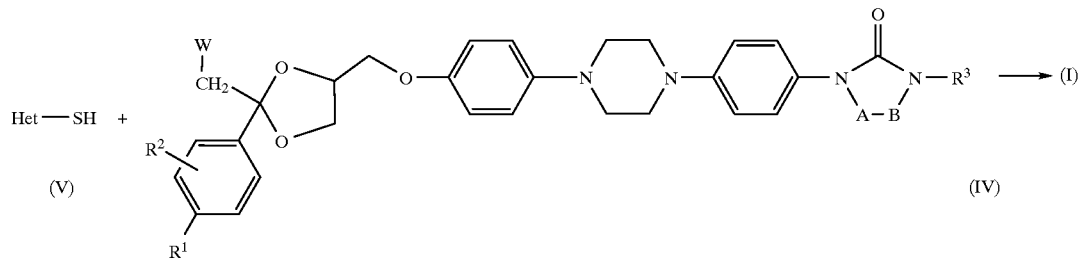

Said reaction may be performed by stirring an heating the intermediates in an appropriate solvent such as a dipolar aprotic solvent, e.g. N,N-dimethylformamide, N,N-dimethylacetamide, dimethylsulfoxide, in the presence of a base such as, an alkali metal carbonate or hydroxide, e.g. sodium or potassium carbonate, or sodium or potassium hydroxide.

Compounds of formula (I) may also be converted into each other. For instance, the compounds wherein $R^3$ is $C_{1-8}$alkyl substituted with hydroxy may be prepared by reduction of the corresponding compounds of formula (I) wherein $R^3$ is $C_{1-8}$alkyl substituted with oxo. The compounds of formula (I) wherein an endocyclic or exocyclic nitrogen atom of the heterocyclic radical "Het" is substituted with a $C_{1-6}$alkyl may be prepared from the corresponding compounds wherein said endocyclic or exocyclic nitrogen atom is unsubstituted by art-known N-alkylation reactions. The compounds of formula (I) wherein $R^3$ is other than hydrogen may be prepared from compounds of formula (I) wherein $R^3$ is hydrogen by art-known N-alkylation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates of formula (III), which are deemed novel, may be prepared by the following rectionsequence. A heterocyclic reagent (V) is S-alkylated with an intermediate of formula (VI), wherein W is an appropriate leaving group as defined hereinabove, by stirring and heating the intermediates in an appropriate reaction-inert solvent such as a ketone, e.g. acetone, in the presence of a base such as a alkali metal carbonate or hydoxide, e.g. sodium or potassium carbonate, sodium or potassium hydroxide. The thus formed ketone of formula (VII) is then converted into the corresponding ketal of formula (VIII) by stirring and heating the intermediate of formula (VII) with glycerol in the presence of an acid such as for example p-toluenesulfonic acid in a reaction inert solvent such as toluene. Finally, the hydroxylfunction of the intermediate of formula (VIII) is converted into an appropriate leaving group by art-known functional group transformation reations, such as, for example, converting the hydroxyl group into a tosylate by reaction with p-toluenesulfonylchloride.

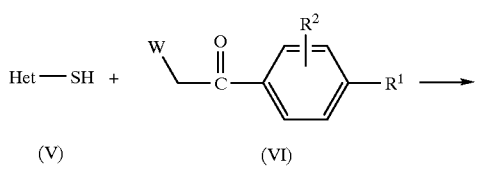

(V)  (VI)

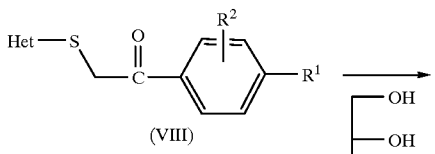

(VII)

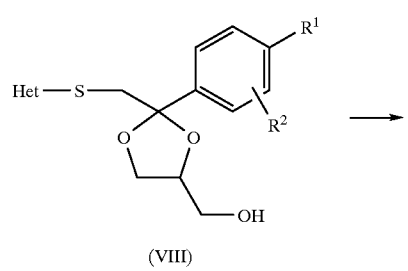

(VIII)

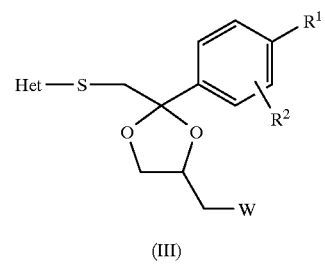

(III)

The intermediates of formula (IV) may be prepared be prepared in an analogous way.

An intermediate of formula (VI) is ketalized as described hereinabove. Subsequently, the hydroxyl function is converted into an appropriate leaving group, e.g. a sulfonyloxy group. Reaction of the thus formed intermediate (IX) with an intermediate (II) results in an intermediate (IV).

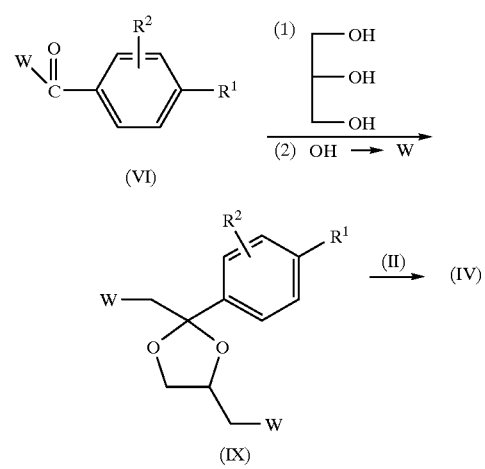

Pure stereochemically isomeric forms of the compounds of formula (I) may be obtained by the application of art-known procedures. Diastereomers may be separated by physical separation methods such as selective crystallization and chromatographic techniques, e.g. liquid chromatography. Enantiomers may be separated from each other by forming diastereomeric salt forms with optically pure chiral acids and subsequent selective crystallization. Said pure stereochemically isomeric forms may also be prepared from the corresponding stereochemically isomeric forms of the appropriate starting materials, provided that the reaction occurs stereospecifically. Preferably if a specific stereochemically isomeric form is desired, said form will be synthesized by stereospecific methods of preparation. These methods will advantageously employ enantiomerically pure starting materials.

The present compounds inhibit the synthesis of apolipoprotein B as can be evidenced by the results obtained in the "Apolipoprotein B (apo B) inhibition test" as described hereinafter. Apolipoprotein B is the principal protein component of very low density lipoproteins (VLDL) and low density lipoproteins (LDL). Approximately 60 to 70% of the total serum cholesterol is transported in LDL. Increased concentration of LDL-cholesterol in serum is causally related to atherosclerosis. By inhibiting the synthesis of apolipoprotein B the amount of noxious low density lipoproteins is decreased.

The present compounds show no or little undesired side-effects such as, for example, albumine inhibiting activity, androgen biosynthesis inhibiting activity or cholesterol biosynthesis inhibiting activity.

In view of their apolipoprotein B inhibiting activity and concommitant lipid lowering activity the present compounds are useful as a medicine especially in a method of treating patients suffering from hyperlipidemia. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL. A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrofic syndrome, cholestasis and bulimia. Primary hyperlipidemias are common hypercholesterolaemia, familial combined hyperlipidaemia, familial hypercholesterolaemia, remnant hyperlipidaemia, chylomicronaemai syndrome, familial hypertriglyceridaemia. The present compounds may also be used to prevent or treat patients suffering from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of their apolipoproteine B inhibiting activity the subject compounds may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier. Said carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of the compounds of formula (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in the treatment of hyperlipidemia could easily determine the effective daily amount from the test results presented hereinafter. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 5 mg of active ingredient per unit dosage form.

The exact dosage and frequency of administration depends on the particular compound of formula (I) used, the particular condition being treated, the severity of the condition being treated, the age, weight and general physical condition of the particular patient as well as other other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.
Experimental part Hereinafter, the term "DIPE" means diisopropylether, "MIK" means methylisopropyl ketone and "DMF" means N,N-dimethylformamide.

A. Preparation of the intermediates

EXAMPLE 1 a) A mixture of 1-methyl-1H-1,2,4-triazole-5-thiol (35 g), 2-chloro-1-(fluorophenyl)-ethanone (51.4 g) and sodium carbonate (32.5 g) in 2-propanone (500 ml) was stirred and refluxed for 4 hours. The solvent was evaporated, the residue was dissolved in $CH_2Cl_2$, filtered and the filtrate evaporated. The residue was crystallized from DIPE, yielding 25 g (33%) of product. A sample (3 g) was purified by column chromatography over silica gel (eluent: $CH_2Cl_2/CH_3OH$ 99/1). The pure fractions were collected and evaporated. The residue was crystallized from DIPE, yielding 1-(4-fluorophenyl)-2-[(2-methyl-2H-1,2,4-triazol-3-yl)thio]ethanone (interm. 1).

b) A mixture of intermediate (1) (22 g), glycerol (39.6 g) and p-toluenesulfonic acid (20 g) in toluene (200 ml) was stirred and refluxed overnight. The mixture was cooled and water was added. The mixture was extracted with toluene and washed with water. The organic layer was dried, filtered and the solvent evaporated. The residue was purified by HPLC over silica gel (eluent: $CH_2Cl_2/CH_3OH$ 98/2). The pure fractions were collected and evaporated, yielding 9 g (31.6%) of (±)-cis-2-(4-fluorophenyl)-2-[[(2-methyl-2H-1,2,4-triazol-3-yl)thio]methyl]-1,3-dioxolane-4-methanol (interm. 2).

c) A mixture of intermediate (2) (9 g), p-toluene sulfonyl chloride (6.3 g) and N,N-dimethyl-4-pyridinamine (1 g) in $CH_2Cl_2$ (150 ml) and N,N-diethylethanamine (5 ml) was stirred at room temperature for 4 hours. Water was added and the layers were separated. The organic layer was washed with water, dried, filtered and the solvent evaporated. The residue was purified by column chromatography over silica gel (eluent: $CH_2Cl_2/CH_3OH$ 99/1). The pure fractions were collected and evaporated at a temperature<35° C. The residue was dissolved in MIK and converted into the p-toluenesulfonic acid salt (1:1). A little DIPE was added and the product was crystallized out. The precipitate was filtered off and dried, yielding 6.8 g (37.8%) of (±)-cis-2-(4-fluorophenyl)-2-[[(2-methyl-2H-1,2,4-triazol-3-yl)thio]methyl]-1,3-dioxolane-4-methanol 4-methylbenzenesulfonate 4-methylbenzenesulfonate (1:1) (interm. 3).

In a similar matter were also prepared:

(±)-cis-2-(4-fluorophenyl)-2-[[(4-methyl-4H-1,2,4-triazol-3-yl)thio]methyl]-1,3-dioxolan-4-methanol 4-methylbenzenesulfonate(ester) 4-methylbenzenesulfonate(1:1); mp. 136.4° C. (interm. 4);

(±)-cis-2-(2,4-difluorophenyl)-2-[[(4-methyl-4H-1,2,4-triazol-3-yl)thio]methyl]-1,3-dioxolane-4-methanol 4-methylbenzenesulfonate(ester) 4-methylbenzenesulfonate (1:1) (interm. 5);

(±)-trans-2-(4-chlorophenyl)-2-[[(4-methyl-4H-1,2,4-triazol-3-yl)thio]methyl]-1,3-dioxolane-4-methanol 4-methylbenzenesulfonate(ester) 4-methylbenzenesulfonate (1:1); mp. 151.9° C. (interm. 6);

(±)-cis-2-(2,4-difluorophenyl)-2-[[(2-methyl-2H-1,2,4-triazol-3-yl)thio]methyl]-1,3-dioxolane-4-methanol 4-methylbenzenesulfonate (ester) (interm. 7); and (±)-cis-[2-(bromomethyl)-2-(2,4-difluorophenyl)-1,3-dioxolan-4-yl]methyl 2-naphthalenesulfonate (interm. 40).

EXAMPLE 2 a) A mixture of 2-bromo-1-(4-chlorophenyl)ethanone (350 g), glycerine (322 g) and p-toluenesulfonic acid (35 g) in toluene (3000 ml) was stirred and refluxed for 24 hours, using a water separator. The reaction mixture was poured into an aqueous $NaHCO_3$ solution and stirred for a while. The organic layer was separated, dried, filtered and the solvent was evaporated, yielding 485 g (93%; oil) of (cis+trans)-2-(bromomethyl)-2-(4-chlorophenyl)-1,3-dioxolane-4-methanol (interm. 8a). 2-Napthalenesulfonyl chloride (21 g) was added portionwise to a mixture of intermediate (8a) (25 g) and N,N-dimethyl-4-pyridinamine (1 g) in N,N-diethylethanamine (25 ml) and $CH_2Cl_2$ (250 ml) and the mixture was stirred at room temperature for 2 hours. The mixture was poured into water and washed. The organic layer was dried, filtered and the solvent evaporated. The residue was purified by column chromatography over silica gel (eluent: $CH_2Cl_2/CH_3OH$ 99/1). The pure fractions were collected and evaporated. The residue was purified by column chromatography (eluent: $CH_2Cl_2$/hexane 40/60 to 60/40). The pure fractions were collected and evaporated, yielding 21.8 g (55%) of (±)-cis-[2-(bromomethyl)-2-(4-chlorophenyl)-1,3-dioxolan-4-yl]methyl 2-naphthalenesulfonate (interm. 8b).

c) 2,4-dihydro-4-[4-[4-(4-hydroxyphenyl)-1-piperazinyl]phenyl]-2-(1-methylpropyl)-3H-1,2,4-triazol-3-one (206.9 g) was added to a solution of intermediate (8b) (250 g) in dimethyl sulfoxide (2000 ml). Potassium hydroxide (67 g) was added and the reaction mixture was stirred overnight at room temperature. The mixture was poured into water (3000 ml) and stirred for 30 minutes. The precipitate was filtered off, washed with 2-propanol (1000 ml) and DIPE (1000 ml), then dried, yielding 316 g (92.2%) of (±)-cis-4-[4-[4-[4-[[2-(bromomethyl)-2-(4-chlorophenyl)-1,3-dioxolan-4-yl]methoxy]phenyl]-1-piperazinyl]phenyl]-2,4-dihydro-2-(1-methylpropyl)-3H-1,2,4-triazol-3-one (interm. 8c).

In a similar manner were prepared:

TABLE 1

| Int. No. | R¹ | R² | A—B | R³ | Physical data |
|---|---|---|---|---|---|
| 8c | Cl | H | CH=N | $CH(CH_3)CH_2CH_3$ | cis |
| 9 | Cl | H | N=CH | $CH(CH_3)_2$ | mp. 185.8° C.; cis |
| 10 | Cl | H | CH=N | $CH_2CH(CH_3)_2$ | mp. 168.3° C.; cis |
| 11 | Cl | H | N=CH | $CH_2CH(CH_3)_2$ | mp. 175.6° C.; cis |
| 12 | Cl | H | N=CH | $CH(CH_3)CH_2CH_3$ | mp. 172.6° C.; cis |
| 13 | Cl | H | N=CH | $CH(CH_2CH_3)_2$ | mp. 164.3° C.; cis |
| 14 | Cl | H | N=CH | $(CH_2)_2CH_3$ | mp. 201.9° C.; cis |
| 15 | Cl | H | N=CH | $(CH_2)_3CH_3$ | mp. 153.8° C.; cis |
| 16 | Cl | H | CH=N | $cycloC_5H_9$ | cis |
| 17 | Cl | H | CH=N | $(CH_2)_3CH_3$ | mp. 172.0° C.; cis |
| 18 | Cl | H | N=CH | $CH_2CH_3$ | mp. 186.3° C.; cis |

TABLE 1-continued

Structure: Br—CH₂ group on benzene ring with R² and R¹, connected via dioxolane CH₂—O—phenyl—N(piperazine)N—phenyl—N(triazolone with A=B and R³)

| Int. No. | R¹ | R² | A—B | R³ | Physical data |
|---|---|---|---|---|---|
| 19 | Cl | H | N=CH | (CH₂)₄CH₃ | mp. 164.7° C.; cis |
| 20 | Cl | H | CH=N | (CH₂)₂CH₃ | mp. 172.9° C.; cis |
| 21 | Cl | H | CH=N | CH₂CH₃ | mp. 186.6° C.; cis |
| 22 | Cl | H | N=CH | CH₃ | mp. 203.9° C.; cis |
| 23 | Cl | H | CH=N | CH₃ | cis |
| 24 | Cl | H | CH=N | CH(CH₃)CH₂CH₃ | [2S-[2α,4α(R*)]] |
| 25 | Cl | H | CH=N | CH(CH₃)CH₂CH₃ | [2R-[2α,4α(S*)]] |
| 26 | Cl | H | CH=N | CH(CH₃)CH₂CH₃ | [2S-[2α,4α(S*)]] |
| 27 | Cl | H | CH=N | CH(CH₃)CH₂CH₃ | [2R-[2α,4α(R*)]] |
| 28 | F | H | CH=N | (CH₂)₂CH(CH₃)₂ | mp. 170.3° C.; cis |
| 29 | F | H | CH=N | CH(CH₂CH₃)₂ | cis |
| 30 | F | H | CH=N | CH(CH₃)CH₂CH₃ | mp. 152.98° C.; cis |
| 31 | F | H | N=CH | CH(CH₃)C₂CH₃ | mp. 174.2° C.; cis |
| 32 | F | F | CH=N | CH(CH₂CH₃)₂ | cis |
| 33 | Cl | H | C(CH₃)₂CO | CH(CH₃)CH₂CH₃ | cis |
| 34 | Cl | H | COC(CH₃)₃ | CH(CH₃)CH₂CH₃ | cis |
| 35 | Cl | H | C(CH₃)=N | CH(CH₃)CH₂CH₃ | cis |
| 36 | F | H | CH=N | cycloC₅H₉ | cis |
| 37 | F | H | N=CH | cycloC₅H₉ | cis |
| 38 | F | H | N=CH | CH(CH₂CH₃)₂ | cis |
| 39 | F | F | CH=N | cycloC₅H₉ | cis |
| 40 | F | H | CH=CH | CH(CH₃)CH₂CH₃ | cis |
| 41 | Cl | H | CH=CH | CH(C₂H₅)CH₂CH₃ | mp. 169.8° C.; cis |
| 42 | Cl | H | CH=CH | cycloC₅H₉ | mp. 192.7° C.; cis |
| 43 | F | H | N=CH | (CH₂)₄CH₃ | cis |
| 44 | Cl | H | N=CH | cycloC₅H₉ | mp. 192.3° C.; 2S-cis |
| 45 | Cl | H | N=CH | (CH₂)₄CH₃ | 2S-cis |

B. Preparation of the final compounds

EXAMPLE 3

A mixture of 4-methyl-4H-1,2,4-triazole-3-thiol (1.9 g), intermediate (8c) (9 g) and sodium carbonate (3 g) in DMF (150 ml) was stirred under N₂ at 120° C. overnight. The mixture was cooled, diluted with water and the product was crystallized out. The precipitate was filtered off and purified by column chromatography over silica gel (eluent: CH₂Cl₂/n-hexane/EtOAc/CH₃OH 500/250/250/2). The pure fractions were collected and evaporated. The residue was triturated in CH₃OH and recrystallized from n-C₄H₉OH, yielding 6.3 g of (±)-cis-4-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]-phenyl]-2,4-dihydro-2-(1-methylpropyl)-3H-1,2,4-triazol-3-one (68%); mp. 173° C. (compound 22).

EXAMPLE 4

A mixture of intermediate (3) (3.3 g), 2,4-dihydro-2-[4-[4-(4-hydroxyphenyl)-1-piperazinyl]phenyl]-4-(1-methylpropyl)-3H-1,2,4-triazol-3-one (2 g) and potassium hydroxide (1 g) in DMF (100 ml) was stirred at room temperature under N₂ for 6 hours. Intermediate (3) (1 g) was added again and the mixture was stirred for 1 hour. The mixture was poured into water and filtered. The precipitate was purified by column chromatography over silica gel (eluent: CH₂Cl₂/CH₃OH 99/1). The pure fractions were collected and evaporated. The residue was crystallized from MIK, yielding 1.6 g of (±)-cis-2-[4-[4-[4-[[2-(4-fluorophenyl)-2-[[(2-methyl-2H-1,2,4-triazol-3-yl)thio]methyl]-1,3-dioxolan-4-yl]methoxyl]phenyl]-1-piperazinyl]phenyl]-2,4-dihydro-4-(1-methylpropyl)-3H-1,2,4-triazol-3-one (45.7%); mp. 157.3° C. (compound 70).

EXAMPLE 5

Sodium hydride, 50%, dispersion in mineral oil (0.31 g) was added to a mixture of compound (76) (4.3 g) in DMF (100 ml) and the mixture was stirred at room temperature for 30 minutes. 2-Bromopropane (0.86 g) was added and the mixture was stirred at room temperature for 48 hours. Sodium hydride, 50%, dispersion in mineral oil and 2-bromopropane were added again and the mixture was stirred for 4 hours. The mixture was poured into water, extracted with CH₂Cl₂ and washed with water. The organic layer was dried, filtered and the solvent evaporated. The residue was purified by column chromatography over silica gel (eluent: CH₂Cl₂/CH₃OH 99/1). The pure fractions were collected and evaporated. The residue was crystallized from CH₃OH. The residue was purified by HPLC. The pure fractions were collected and evaporated. Fraction 1 was crystallized from n-C₄H₉OH, yielding 0.4 g of (±)-cis-4-[4-[4-[4-[[2-(4-chlorophenyl)-2-[[[1-(1-methylethyl)-1H-1,2,4-triazol-3-yl]thio]methyl]-1,3-dioxolan- 4-yl]methoxy]phenyl]-1-piperazinyl]phenyl]-2,4-dihydro-2-(1-methylpropyl)-3H-1,2,4-triazol-3-one; mp. 128.8° C. (compound 112). Fraction 2 was triturated in CH₃OH, yielding 1.4 g of (±)-cis-4-[4-[4-[4-[[2-(4-chlorophenyl)-2-[[[2-(1-methylethyl)-2H-1,2,4-triazol-3-yl]thio]methyl]-1,3-dioxolan-4-yl]methoxy]phenyl]-1-piperazinyl]hexyl]-2,4-dihydro-2-(1-methylpropyl)-3H-1,2,4-triazol-3-one; mp. 141.2° C. (compound 82).

EXAMPLE 6

A solution of sodium borohydride (1 g) in water (20 ml) was added dropwise to a solution of compound (47) (3.6 g) in DMF (100 ml). The reaction mixture was stirred overnight at room temperature. Acetic acid (1 ml) was added. Water (750 ml) was added, resulting in crystallization of the product. The residue was purified by column chromatography over silica gel (eluent: CH₂Cl₂/CH₃OH 90/10). The pure fractions were collected and the solvent was evaporated. The residue was triturated in 2-propanol. The precipitate was filtered off and dried, yielding 2.9 g of (±)-cis-4-[4-[4-[4-[[2-(4-chlorophenyl)-2-[[(4methyl-4H-1,2,4-triazol-3-yl)thio]methyl]-1,3-dioxolan-4-yl]methoxy]phenyl]-1-piperazinyl]phenyl]-2,4-dihydro-2-(2-hydroxy-1-methylpropyl)-3H-1,2,4-triazol-3-one; mp. 153.4° C. (compound 48).

TABLE 2

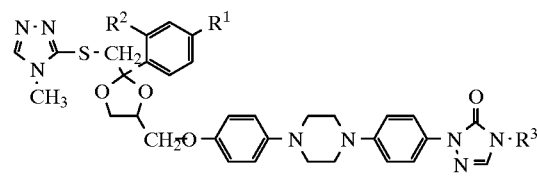

| Co. No | Ex. No | R¹ | R² | R³ | physical data |
|---|---|---|---|---|---|
| 1 | 3 | Cl | H | CH(CH₃)₂ | mp. 194.8° C./cis |
| 2 | 3 | Cl | H | CH(CH₃)CH₂CH₃ | mp. 147.8° C./cis |
| 3 | 3 | Cl | H | CH₂—CH(CH₃)₂ | mp. 182.5° C./cis |
| 4 | 4 | F | H | CH(CH₃)₂ | mp. 181.1° C./cis |
| 5 | 4 | F | H | CH₂—CH(CH₃)₂ | mp. 166.4° C./cis |
| 6 | 3 | Cl | H | cyclo(C₅H₉) | mp. 198.8° C./cis |
| 7 | 3 | Cl | H | CH(CH₂CH₃)₂ | mp. 139.6° C./cis |
| 8 | 3 | Cl | H | (CH₂)₂CH₃ | mp. 184.6° C./cis |
| 9 | 4 | F | H | CH(CH₃)CH₂CH₃ | mp. 180.0° C./cis |
| 10 | 4 | F | F | CH(CH₃)CH₂CH₃ | mp. 180.7° C./cis |
| 11 | 4 | F | H | cyclo(C₅H₉) | mp. 194.2° C./cis |
| 12 | 4 | F | H | CH(CH₂CH₃)₂ | mp. 144.3° C./cis |
| 13 | 4 | F | F | cyclo(C₅H₉) | mp. 202.4° C./cis |
| 14 | 4 | F | F | CH(CH₂CH₃)₂ | mp. 166.7° C./cis |
| 15 | 3 | Cl | H | (CH₂)₃CH₃ | mp. 194.6° C./cis |
| 16 | 3 | Cl | H | CH₂—CH₃ | mp. 218.3° C./cis |
| 17 | 3 | Cl | H | CH₂—CH(OH)—C(CH₃)₃ | mp. 205.9° C./cis |
| 18 | 3 | Cl | H | (CH₂)₄CH₃ | mp. 173.8° C./cis |
| 19 | 4 | Cl | H | CH(CH₃)CH₂CH₃ | mp. 140.9° C./cis |
| 20 | 4 | Cl | H | CH₃ | mp. 208.6° C./trans |

TABLE 2-continued

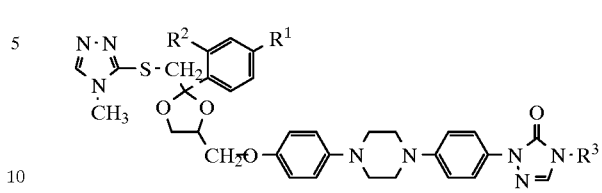

| Co. No | Ex. No | R¹ | R² | R³ | physical data |
|---|---|---|---|---|---|
| 21 | 4 | Cl | | CH(CH₃)CH(OH)(CH₃) | mp. 202.4° C./cis |
| 133 | 3 | CH₃ | H | (CH₂)₄CH₃ | mp. 147.4° C./cis |
| 134 | 3 | Br | H | (CH₂)₄CH₃ | mp. 152.5° C./cis |
| 136 | 3 | Cl | H | cyclo(C₅H₉) | 2S-cis |
| 137 | 3 | Cl | H | (CH₂)₄CH₃ | 2S-cis |

TABLE 3

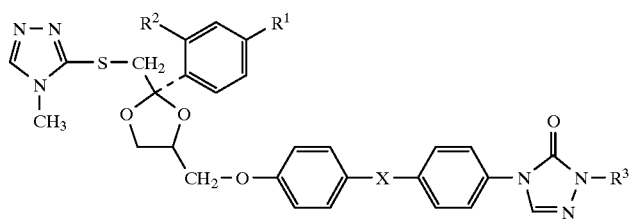

| Co. No | Ex. No | R¹ | R² | R³ | —X— | physical data |
|---|---|---|---|---|---|---|
| 22 | 3 | Cl | H | CH(CH₃)CH₂CH₃ | —N(CH₂CH₂)₂N— | mp. 176.9° C./cis |
| 23 | 3 | Cl | H | CH₂CH(CH₃)₂ | —N(CH₂CH₂)₂N— | mp. 192.9° C./cis |
| 24 | 3 | Cl | H | cyclo(C₅H₉) | —N(CH₂CH₂)₂N— | mp. 210.2° C./cis |

TABLE 3-continued

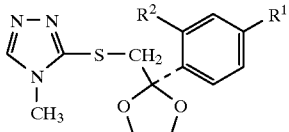

| Co. No | Ex. No. | R1 | R² | R³ | —X— | physical data |
|---|---|---|---|---|---|---|
| 25 | 4 | F | H | CH₂CH(CH₃)₂ | piperazine | mp. 180.6° C./cis |
| 26 | 3 | Cl | H | (CH₂)₃CH₃ | piperazine | mp. 194.1° C./cis |
| 27 | 3 | Cl | H | (CH₂)₂CH₃ | piperazine | mp. 187.3° C./cis |
| 28 | 4 | F | H | CH(CH₃)CH₂CH₃ | piperazine | mp. 157.5° C./cis |
| 29 | 4 | F | F | CH(CH₃)CH₂CH₃ | piperazine | mp. 146.4° C./cis |
| 30 | 3 | Cl | H | CH₂—CH₃ | piperazine | mp. 195.5° C./cis |
| 31 | 3 | Cl | H | CH₃ | piperazine | mp. 161.2° C./cis |
| 32 | 4 | Cl | H | (CH₂)₄CH₃ | piperazine | mp. 191.7° C./cis |
| 33 | 4 | Cl | H | CH(CH₃)₂ | piperazine | mp. 157.2° C./cis |
| 34 | 4 | Cl | H | CH₂—CH(OH)—C(CH₃)₃ | piperazine | mp. 189.9° C./cis |

TABLE 3-continued

| Co. No | Ex. No. | R¹ | R² | R³ | —X— | physical data |
|---|---|---|---|---|---|---|
| 35 | 4 | F | H | cyclo($C_5H_9$) |  | mp. 198.2° C./cis |
| 36 | 4 | Cl | H | $CH(CH_3)CH_2CH_3$ |  | mp. 180.7° C./cis |
| 37 | 4 | F | F | cyclo($C_5H_9$) |  | mp. 185.2° C./cis |
| 38 | 3 | Cl | H | $CH(CH_3)CH_2CH_3$ | 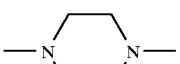 | mp. 187.0° C./<br>$[\alpha]_D^{20} = -24.5°$<br>(c = 0.5% in DMF)<br>(−)-[2S-[2α,4α(R*)]] |
| 39 | 3 | Cl | H | $CH(CH_3)CH_2CH_3$ | 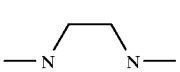 | mp. 155.1° C./<br>$[\alpha]_D^{20} = +34.64°$<br>(c = 0.5% in DMF)<br>(+)-[2R-[2α,4α(S*)]] |
| 40 | 3 | Cl | H | $CH(CH_3)CH_2CH_3$ | 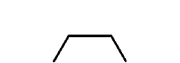 | mp. 156.4° C./<br>$[\alpha]_D^{20} = -33.1°$<br>(c = 0.5% in DMF)<br>(−)-[2S-[2α,4α(S*)]] |
| 41 | 3 | Cl | H | $CH(CH_3)CH_2CH_3$ | 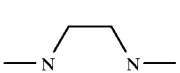 | mp. 187.7° C./<br>$[\alpha]_D^{20} = +24.65°$<br>(c = 0.5% in DMF)<br>(+)-[2R-[2α,4α(R*)]] |
| 42 | 3 | F | H | $(CH_2)_2CH(CH_3)_2$ | 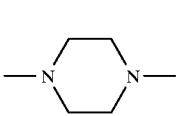 | mp. 176.4° C./cis |
| 43 | 3 | F | H | $CH(CH_2CH_3)_2$ |  | mp. 145.6° C./cis |
| 44 | 4 | Cl | H | $CH(CH_2CH_3)_2$ | | mp. 156.7° C./cis |

TABLE 3-continued

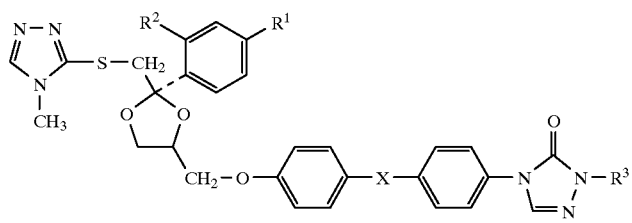

| Co. No | Ex. No. | R1 | R2 | R3 | —X— | physical data |
|---|---|---|---|---|---|---|
| 45 | 4 | F | F | (CH₂)₂CH(CH₃)₂ | piperazine | mp. 176.8° C./cis |
| 46 | 3 | F | F | CH(CH₂CH₃)₂ | piperazine | mp. 118.6° C./cis |
| 47 | 4 | Cl | H | CH(CH₃)COCH₃ | piperazine | mp. 157.6° C./cis |
| 48 | 6 | Cl | H | CH(CH₃)CH(OH)CH₃ | piperazine | mp. 153.4° C./cis |
| 135 | 3 | Cl | H | CH(CH₃)CH₂CH₃ | N-oxide piperazine | cis |

TABLE 4

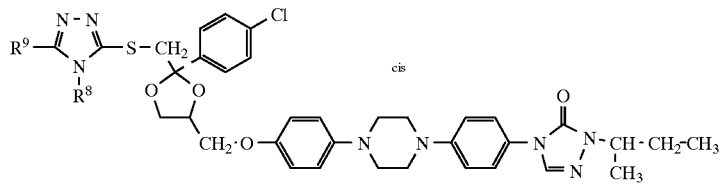

| Co. No. | Ex. No. | R9 | R8 | physical data |
|---|---|---|---|---|
| 49 | 3 | CF₃ | H | mp. 133.3° C. |
| 50 | 3 | CF₃ | CH₃ | mp. 159.6° C. |
| 51 | 3 | H | (CH₂)₃CH₃ | mp. 173.5° C. |
| 52 | 3 | H | CH(CH₃)₂ | mp. 159.1° C. |
| 53 | 3 | H | CH₂CH₃ | mp. 175.6° C. |
| 54 | 3 | H | CH₂CH(CH₃)₂ | mp. 186.4° C. |
| 55 | 3 | H | (CH₂)₂CH₃ | mp. 168.5° C. |
| 56 | 3 | CH₃ | CH₃ | mp. 170.0° C. |
| 57 | 3 | NH₂ | H | — |
| 58 | 3 | OH | CH₃ | — |
| 59 | 3 | OH | CH(CH₃)₂ | — |

TABLE 5

| Co. No. | Ex. No. | R¹ | R² | R³ | A—B | physical data |
|---|---|---|---|---|---|---|
| 60 | 3 | Cl | H | $CH(CH_3)CH_2CH_3$ | CH=N | mp. 147.7° C. |
| 61 | 3 | Cl | H | $CH_2CH(CH_3)_2$ | CH=N | mp. 159.4° C. |
| 62 | 4 | F | F | $CH(CH_3)CH_2CH_3$ | CH=N | mp. 100.6° C. |
| 63 | 4 | F | H | $CH(CH_3)CH_2CH_3$ | CH=N | mp. 138.8° C. |
| 64 | 3 | F | H | $CH(CH_2CH_3)_2$ | CH=N | mp. 132.3° C. |
| 65 | 3 | F | F | $CH(CH_2CH_3)_2$ | CH=N | mp. 120.4° C. |
| 66 | 3 | F | H | $cyclo(C_5H_9)$ | CH=N | mp. 163.0° C. |
| 67 | 3 | F | F | $cyclo(C_5H_9)$ | CH=N | mp. 150.7° C. |
| 68 | 3 | Cl | H | $CH(CH_3)_2$ | N=CH | mp. 170.1° C. |
| 69 | 3 | Cl | H | $CH(CH_3)CH_2CH_3$ | N=CH | mp. 176.2° C. |
| 70 | 4 | F | H | $CH(CH_3)CH_2CH_3$ | N=CH | mp. 157.3° C. |
| 71 | 4 | F | F | $CH(CH_3)CH_2CH_3$ | N=CH | mp. 162.4° C. |
| 72 | 4 | F | F | $cyclo(C_5H_9)$ | N=CH | mp. 183.3° C. |
| 73 | 4 | F | F | $CH(CH_2CH_3)_2$ | N=CH | mp. 158.9° C. |
| 74 | 3 | F | H | $cyclo(C_5H_9)$ | N=CH | mp. 201.2° C. |
| 75 | 3 | F | H | $CH(CH_2CH_3)_2$ | N=CH | mp. 117.4° C. |

TABLE 6

| Co. No. | Ex. No. | R⁹ | R⁸ | R¹ | A—B | R³ | physical data |
|---|---|---|---|---|---|---|---|
| 76 | 3 | H | H | Cl | CH=N | $CH(CH_3)CH_2CH_3$ | mp. 179.6° C. |
| 77 | 3 | H | $CH_2CH_3$ | Cl | CH=N | $CH(CH_3)CH_2CH_3$ | mp. 119.3° C. |
| 78 | 3 | $CH_2CH_3$ | $(CH_2)_2CH_3$ | Cl | CH=N | $CH(CH_3)CH_2CH_3$ | mp. 97.8° C. |
| 79 | 3 | H | $(CH_2)_3CH_3$ | Cl | CH=N | $CH(CH_3)CH_2CH_3$ | mp. 108.6° C. |
| 80 | 3 | H | $(CH_2)_2CH_3$ | Cl | CH=N | $CH(CH_3)CH_2CH_3$ | mp. 87.3° C. |
| 81 | 3 | $CH_3$ | $CH_3$ | Cl | CH=N | $CH(CH_3)CH_2CH_3$ | mp. 85.6° C. |
| 82 | 5 | H | $CH(CH_3)_2$ | Cl | CH=N | $CH(CH_3)CH_2CH_3$ | mp. 141.2° C. |
| 83 | 3 | H | H | Cl | N=CH | $CH(CH_3)CH_2CH_3$ | mp. 160.1° C. |
| 84 | 3 | H | H | Cl | N=CH | $CH_2CH(CH_3)_2$ | mp. 160.6° C. |
| 85 | 5 | H | $CH(CH_3)_2$ | Cl | N=CH | $CH(CH_3)CH_2CH_3$ | mp. 134.9° C. |
| 86 | 3 | H | H | F | CH=N | $CH(CH_3)CH_2CH_3$ | mp. 101.3° C. |
| 87 | 3 | H | $CH_3$ | Cl | N=CH | $CH_2CH(CH_3)_2$ | mp. 154.3° C. |
| 114 | 3 | H | $CH_3$ | Cl | CH=CH | $CH(CH_3)CH_2CH_3$ | mp. 125.2° C. |
| 115 | 3 | H | $CH_3$ | Cl | CH=CH | $CH(C_2H_5)CH_2CH_3$ | mp. 147.7° C. |
| 116 | 3 | H | $CH_3$ | Cl | CH=CH | $cyclo(C_5H_9)$ | mp. 154.2° C. |
| 117 | 3 | H | H | Cl | CH=CH | $CH(CH_3)CH_2CH_3$ | mp. 186.8° C. |
| 118 | 3 | H | $CH_3$ | F | CH=CH | $CH(C_2H_5)CH_2CH_3$ | mp. 134.1° C. |
| 119 | 3 | H | $CH_3$ | Cl | CH=N | $cyclo(C_5H_9)$ | mp. 161.1° C. |
| 120 | 5 | H | $CH(CH_3)_2$ | Cl | CH=CH | $CH(CH_3)CH_2CH_3$ | mp. 137.5° C. |
| 121 | 3 | H | $CH_3$ | F | CH=CH | $cyclo(C_5H_9)$ | mp. 166.2° C. |

TABLE 7
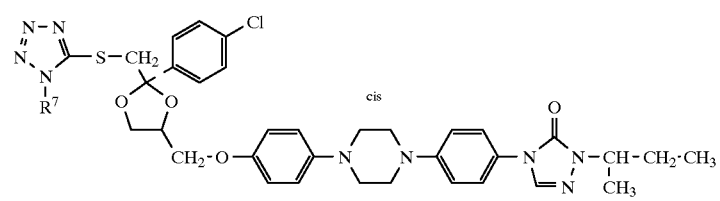
| Co. No. | Ex. No. | R⁷ | physical data |
|---|---|---|---|
| 88 | 3 | CH₃ | — |
| 89 | 3 | phenyl | — |
TABLE 8
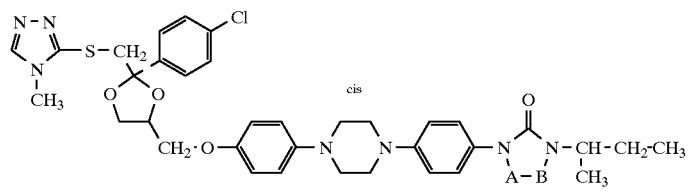
| Co. No. | Ex. No. | A—B | physical data |
|---|---|---|---|
| 90 | 3 | C(CH₃)=N | mp. 98.3° C./½H₂O |
| 91 | 3 | C(CH₃)₂CO | mp. 96.0° C. |
| 92 | 3 | CO—C(CH₃)₂ | mp. 127.1° C. |
| 93 | 4 | CH=CH | mp. 171.8° C. |
| 94 | 4 | CH₂—CH₂ | mp. 147.3° C. |
TABLE 9
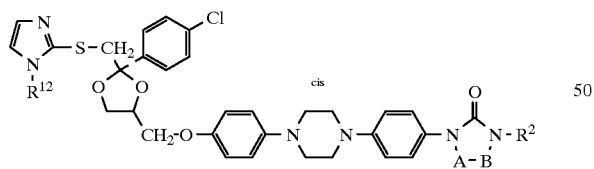
| Co. No. | Ex. No. | R¹² | A—B | R² | physical data |
|---|---|---|---|---|---|
| 95 | 3 | CH₃ | CH=N | CH(CH₃)CH₂CH₃ | mp. 134.2° C. |
| 96 | 3 | CH₃ | CH=N | CH₂CH(CH₃)₂ | mp. 164.9° C. |
| 97 | 3 | H | CH=N | CH(CH₃)CH₂CH₃ | — |
| 98 | 3 | CH₃ | N=CH | CH(CH₃)₂ | mp. 187.7° C. |
| 99 | 3 | CH₃ | N=CH | CH(CH₃)CH₂CH₃ | mp. 150.4° C. |
| 100 | 3 | CH₃ | N=CH | CH₂CH(CH₃)₂ | mp. 146.8° C. |

TABLE 10

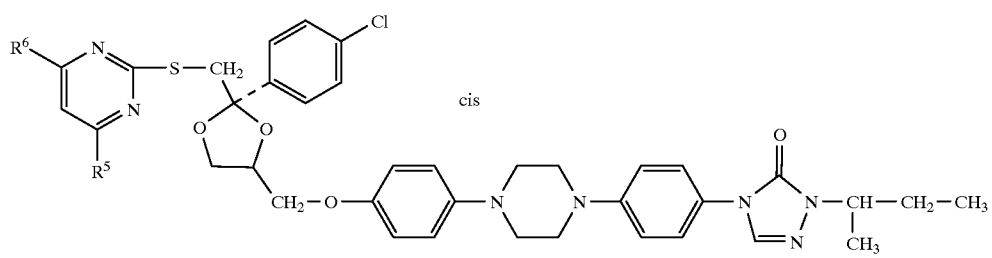

| Co. No. | Ex. No. | R⁵ | R⁶ | physical data |
|---|---|---|---|---|
| 101 | 3 | H | H | mp. 159.6° C. |
| 102 | 3 | CH₃ | CH₃ | mp. 157.4° C. |
| 103 | 3 | NH₂ | NH₂ | mp. 248.5° C. |

TABLE 11

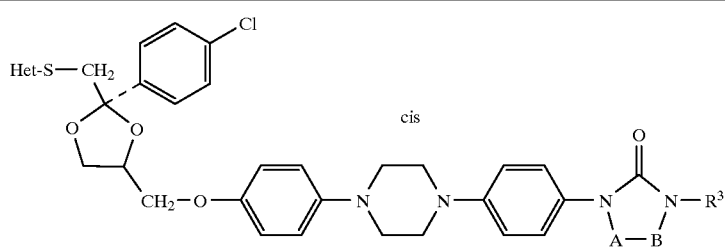

| Co. No. | Ex. No. | Het | A—B | R³ | physical data |
|---|---|---|---|---|---|
| 104 | 3 | 5-methyl-1,3,4-thiadiazol-2-yl | CH=N | CH(CH₃)CH₂CH₃ | — |
| 105 | 3 | 2-pyridinyl | CH—N | CH(CH₃)CH₂CH₃ | mp. 154.1° C. |
| 106 | 3 | 4-pyridinyl | CH=N | CH(CH₃)CH₂CH₃ | mp. 174.9° C. |
| 107 | 3 | 4-methyl-2-oxazolyl | CH=N | CH(CH₃)CH₂CH₃ | mp. 115.3° C. |
| 108 | 3 | 2-thiazolyl | CH=N | CH(CH₃)CH₂CH₃ | mp. 158.6° C. |
| 109 | 3 | 4-oxo-2-thiazolyl | CH=N | CH(CH₃)CH₂CH₃ | — |
| 110 | 3 | 2-thiazolyl | N=CH | CH(CH₃)CH₂CH₃ | mp. 157.8° C. |
| 111 | 3 | 2-thiazolyl | N=CH | CH₂CH(CH₃)₂ | mp. 167.9° C. |
| 112 | 5 | (1-methyl-ethyl)-2H-1,2,4-triazol-3-yl | CH=N | CH(CH₃)CH₂CH₃ | mp. 128.8° C. |
| 113 | 5 | (1-methyl-ethyl)-1H-1,2,4-triazol-3-yl | N=CH | CH(CH₃)CH₂CH₃ | mp. 150.0° C. |
| 122 | 3 | 4-methyl-4H-1,2,4-triazol-3-yl | CH=CH | CH(C₂H₅)CH₂CH₃ | mp. 134.4° C. |
| 123 | 3 | 4-methyl-4H-1,2,4-triazol-3-yl | CH=CH | cyclo(C₅H₉) | mp. 202.8° C. |
| 124 | 5 | (1-methyl-ethyl)-1H-1,2,4-triazol-3-yl | CH=CH | CH(CH₃)CH₂CH₃ | mp. 155.7° C. |
| 125 | 3 | 4-methyl-4H-1,2,4-triazol-3-yl | CH=N | CH(C₂H₅)CH₂CH₃ | mp. 123.2° C. |

TABLE 12

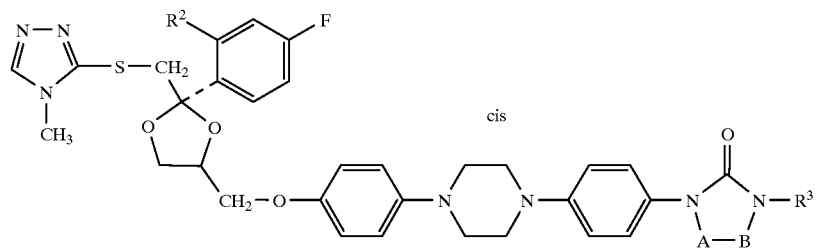

| Co. No. | Ex. No. | $R^2$ | $R^3$ | A—B | physical data |
|---|---|---|---|---|---|
| 126 | 3 | H | CH(CH$_3$)CH$_2$CH$_3$ | CH=CH | mp. 175.4° C. |
| 127 | 3 | F | CH(CH$_3$)CH$_2$CH$_3$ | CH=CH | mp. 155.5° C. |
| 128 | 3 | H | cyclo(C$_5$H$_9$) | CH=CH | mp. 192.0° C. |
| 129 | 3 | F | cyclo(C$_5$H$_9$) | CH=CH | mp. 181.8° C. |
| 130 | 3 | H | CH(C$_2$H$_5$)CH$_2$CH$_3$ | CH=CH | mp. 145.5° C. |
| 131 | 3 | F | CH(C$_2$H$_5$)CH$_2$CH$_3$ | CH=CH | mp. 139.1° C. |
| 132 | 3 | H | (CH$_2$)$_4$CH$_3$ | N=CH | mp. 153.1° C. |

C. Pharmacological example

EXAMPLE 7

Apolipoprotein B (apo B) inhibition test

Cultured human liver cells (Hepg2-cells), which synthesize and secrete low-density lipoproteins, were incubated overnight at 37° C. in a liquid medium containing radioactively labelled leucine. Thus radioactively labelled leucine was incorporated into the apolipoprotein B. The liquid medium was decanted and the apolipoprotein B was isolated by means of a double immunoprecipitation, i.e. first an apolipoprotein B-specific antibody (antibody$_1$) was added to the liquid medium and subsequently a second antibody (antibody$_2$) was added which binds specifically to the apoB-antibody$_1$-complex. The thus formed apoB-antibody$_1$-antibody$_2$ complex precipitated and was isolated by centrifuge. Quantification of the amount of apolipoprotein B synthesized during the night resulted from measuring the radioactivity of the isolated complex. To measure the inhibiting activity of the test compound, that test compound was added to the liquid medium at different concentrations and the concentration of apolipoprotein B synthesized in the presence of a test compound (concentration apoB(after)) was compared to the concentration of apolipoprotein B which was synthesized in the absence of the test compound (concentration apoB(control)). For each experiment the inhibition of apolipoprotein-B formation was expressed as % inhibition=100×(1−concentration of apoB(after)/concentration apoB(control))

When more experiments were carried out for the same concentration, the median value of the inhibition calculated for these experiments was calculated. IC$_{50}$-values (concentration of the drug needed to reduce apoB secretion to 50% of the control) were also computed.

Table 13 lists the IC$_{50}$-values for some of the exemplified compounds of formula (I). Exemplified compounds of formula (I) that are not listed in Table 13, and for which data is available, have an IC$_{50}$-value of 1×10$^{-6}$M or more.

TABLE 13

| Comp. No. | IC$_{50}$ (× 10$^{-8}$ M) | Comp. No. | IC$_{50}$ (× 10$^{-8}$ M) | Comp. No. | IC$_{50}$ (× 10$^{-8}$ M) |
|---|---|---|---|---|---|
| 1 | 9.2 | 54 | 7.9 | 89 | 51 |
| 2 | 4.7 | 55 | 7.8 | 93 | 2.7 |
| 3 | 9.1 | 56 | 23 | 94 | 19 |
| 4 | 26 | 58 | 31 | 95 | 1.8 |
| 5 | 20 | 60 | 4.6 | 96 | 4.7 |
| 6 | 12 | 61 | 8.1 | 98 | 2.0 |
| 7 | 7.9 | 62 | 19 | 99 | 1.5 |
| 8 | 13 | 63 | 4.6 | 100 | 2.1 |
| 9 | 11 | 64 | 16 | 101 | 16 |
| 12 | 19 | 65 | 29 | 102 | 37 |
| 13 | 51 | 66 | 13 | 105 | 9.9 |
| 15 | 4.8 | 67 | 18 | 106 | 88 |
| 18 | 4.1 | 68 | 8.1 | 107 | 4.5 |
| 22 | 7.1 | 69 | 2.6 | 108 | 2.6 |
| 23 | 14 | 71 | 12 | 110 | 2.7 |
| 24 | 5.8 | 72 | 19 | 111 | 6.2 |
| 28 | 9.7 | 73 | 18 | 112 | 98 |
| 32 | 18 | 74 | 14 | 113 | 3.0 |
| 33 | 9.1 | 75 | 12 | 114 | 5.3 |
| 35 | 7.7 | 76 | 2.4 | 115 | 5.7 |
| 37 | 23 | 77 | 7.1 | 116 | 5.8 |
| 38 | 6.5 | 78 | 5.3 | 117 | 1.6 |
| 40 | 2.3 | 79 | 4.6 | 118 | 9.1 |
| 43 | 11 | 80 | 7.2 | 119 | 4.6 |
| 44 | 5.1 | 81 | 4.9 | 121 | 14 |
| 49 | 85 | 82 | 3.1 | 122 | 8.8 |
| 50 | 26 | 83 | 1.5 | 123 | 7.4 |
| 51 | 4.7 | 84 | 2.8 | 126 | 14 |
| 52 | 25 | 87 | 6.9 | 128 | 18 |
| 53 | 8.4 | 88 | 45 | 130 | 14 |

D. Composition examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a N-oxide form, a pharmaceutically acceptable acid addition salt or a stereochemically isomeric form thereof.

EXAMPLE 8

Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 9

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 10

Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinyl-pyrrolidone (Kollidon-K 90) in about 200 ml of water. The wet powder mixture is sieved, dried and sieved again. Then there are added 100 g microcrystalline cellulose (Avicel) and 15 g hydrogenated vegetable oil (Sterotex). The whole is mixed well and compressed into tablets, giving 10,000 tablets, each comprising 10 mg of the active ingredient.

Coating

To a solution of 10 g methyl cellulose (Methocel 60 HG) in 75 ml of denaturated ethanol there is added a solution of 5 g of ethyl cellulose (Ethocel 22 cps) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109) and the whole is homogenated. The tablet cores are coated with the thus obtained mixture in a coating apparatus.

EXAMPLE 11

Injectable solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration (U.S.P. XVII p. 811) and filled in sterile containers.

We claim:
1. A compound of formula

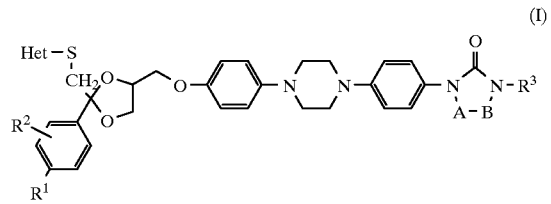

a N-oxide, a stereochemically isomeric form, or a pharmaceutically acceptable acid addition salt thereof, wherein A and B taken together form a bivalent radical of formula:
—N=CH— (a),
—CH=N— (b),
—CH$_2$—CH$_2$— (c),
—CH=CH— (d),
—C(=O)—CH$_2$— (e),
—CH$_2$—C(=O)— (f),
in the bivalent radicals of formula (a) or (b) the hydrogen atom may be replaced by $C_{1-6}$alkyl; in the bivalent radicals of formula (c), (d), (e), (f), one or two hydrogen atoms may be replaced by $C_{1-6}$alkyl;
  $R^1$ is hydrogen, $C_{1-6}$alkyl or halo;
  $R^2$ is hydrogen or halo;
  $R^3$ is hydrogen; $C_{1-8}$alkyl; $C_{3-6}$cycloalkyl; or $C_{1-8}$alkyl substituted with hydroxy, oxo, $C_{3-6}$cycloalkyl or aryl;
  Het is a heterocycle selected from the group consisting of pyridine; pyridine substituted with one or two substituents selected from $C_{1-6}$alkyl, hydroxy, $C_{1-6}$alkyloxy, trihalomethyl, amino, mono- or di($C_{1-6}$alkyl)amino or aryl;
  pyrimidine; pyrimidine substituted with one or two substituents selected from $C_{1-6}$alkyl, hydroxy, $C_{1-6}$alkyloxy, trihalomethyl, amino, mono- or di($C_{1-6}$alkyl)-amino or aryl; tetrazole; tetrazole substituted with $C_{1-6}$alkyl or aryl; triazole; triazole substituted with one or two substituents selected from $C_{1-6}$alkyl, hydroxy, $C_{1-6}$alkyloxy, trihalomethyl, amino, mono- or di($C_{1-6}$alkyl)-amino; thiadiazole;
  thiadiazole substituted with one or two substituents selected from $C_{1-6}$alkyl, hydroxy, $C_{1-6}$alkyloxy, trihalomethyl, amino, mono- or di($C_{1-6}$alkyl)amino; oxadiazole substituted with one or two substituents selected from $C_{1-6}$alkyl, hydroxy, $C_{1-6}$alkyloxy, trihalomethyl, amino, mono- or di($C_{1-6}$alkyl)amino;
  imidazole; imidazole substituted with one or two substituents selected from $C_{1-6}$alkyl, hydroxy, $C_{1-6}$alkyloxy, trihalomethyl, amino, mono- or di($C_{1-6}$alkyl)-amino; thiazole; thiazole substituted with one or two substituents selected from $C_{1-6}$alkyl, hydroxy, $C_{1-6}$alkyloxy, trihalomethyl, amino, mono- or di($C_{1-6}$alkyl)-amino; oxazole; oxazole substituted with one or two substituents selected from $C_{1-6}$alkyl, hydroxy, $C_{1-6}$alkyloxy, trihalomethyl, amino, mono- or di($C_{1-6}$alkyl)-amino; aryl is phenyl or phenyl substituted with $C_{1-6}$alkyl or halo.
2. A compound according to claim 1 wherein $R^1$ is chloro or fluoro.
3. A compound according to claim 1 wherein $R^1$ is methyl.
4. A compound according to claim 1 wherein the bivalent radical —A—B— is —N=CH— or —CH=N—, wherein one hydrogen atom is optionally replaced by $C_{1-6}$alkyl.

5. A compound according to claim 2 wherein the bivalent radical —A—B— is —N=CH— or —CH=N—, wherein one hydrogen atom is optionally replaced by $C_{1-6}$alkyl.

6. A compound according to claim 3 wherein the bivalent radical —A—B— is —N=CH— or —CH=N—, wherein one hydrogen atom is optionally replaced by $C_{1-6}$alkyl.

7. A compound according to claim 1 wherein $R^3$ is butyl, pentyl or cyclopentyl.

8. A compound according to claim 2 wherein $R^3$ is butyl, pentyl or cyclopentyl.

9. A compound according to claim 3 wherein $R^3$ is butyl, pentyl or cyclopentyl.

10. A compound according to claim 4 wherein $R^3$ is butyl, pentyl or cyclopentyl.

11. A compound according to claim 5 wherein $R^3$ is butyl, pentyl or cyclopentyl.

12. A compound according to claim 6 wherein $R^3$ is butyl, pentyl or cyclopentyl.

13. A compound according to claim 1 wherein the compound is selected from the group consisting of:
   cis-2-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-4-(1-methylpropyl)-3H-1,2,4-triazol-3-one;
   cis-2-[4-[4-[4-[[2-(4-fluorophenyl)-2-[[(4-methyl-4H-1,2,4-triazol-3-yl)thio]methyl]-1,3-dioxolan-4-yl]methoxy]phenyl]-1-piperazinyl]phenyl]-4-cyclopentyl-2,4-dihydro-3H-1,2,4-triazol-3-one;
   cis-2-[4-[4-[4-[[2-(4-chlorophenyl)-2-[[(4-methyl-4H-1,2,4-triazol-3-yl)thio]methyl]-1,3-dioxolan-4-yl]methoxy]phenyl]-1-piperazinyl]phenyl]-2,4-dihydro-4-pentyl-3H-1,2,4-triazol-3-one;
   cis-4-(1-ethylpropyl)-2-[4-[4-[4-[[2-(4-fluorophenyl)-2-[[(4-methyl-4H-1,2,4-triazol-3-yl)thio]methyl]-1,3-dioxolan-4-yl]methoxy]-phenyl]-1-piperazinyl]phenyl]-2,4-dihydro-3H-1,2,4-triazol-3-one;
   a pharmaceutically acceptable acid addition salt of the above; and
   a stereochemically isomeric form of the above.

14. A pharmaceutical composition containing a pharmaceutically acceptable carrier and as an active ingredient a therapeutically effective amount of a compound as defined in claim 1.

15. A pharmaceutical composition containing a pharmaceutically acceptable carrier and as an active ingredient a therapeutically effective amount of a compound as defined in claim 2.

16. A pharmaceutical composition containing a pharmaceutically acceptable carrier and as an active ingredient a therapeutically effective amount of a compound as defined in claim 3.

17. A pharmaceutical composition containing a pharmaceutically acceptable carrier and as an active ingredient a therapeutically effective amount of a compound as defined in claim 4.

18. A pharmaceutical composition containing a pharmaceutically acceptable carrier and as an active ingredient a therapeutically effective amount of a compound as defined in claim 5.

19. A pharmaceutical composition containing a pharmaceutically acceptable carrier and as an active ingredient a therapeutically effective amount of a compound as defined in claim 6.

20. A pharmaceutical composition containing a pharmaceutically acceptable carrier and as an active ingredient a therapeutically effective amount of a compound as defined in claim 7.

21. A pharmaceutical composition containing a pharmaceutically acceptable carrier and as an active ingredient a therapeutically effective amount of a compound as defined in claim 8.

22. A pharmaceutical composition containing a pharmaceutically acceptable carrier and as an active ingredient a therapeutically effective amount of a compound as defined in claim 9.

23. A pharmaceutical composition containing a pharmaceutically acceptable carrier and as an active ingredient a therapeutically effective amount of a compound as defined in claim 10.

24. A pharmaceutical composition containing a pharmaceutically acceptable carrier and as an active ingredient a therapeutically effective amount of a compound as defined in claim 11.

25. A pharmaceutical composition containing a pharmaceutically acceptable carrier and as an active ingredient a therapeutically effective amount of a compound as defined in claim 12.

26. A pharmaceutical composition containing a pharmaceutically acceptable carrier and as an active ingredient a therapeutically effective amount of a compound as defined in claim 13.

27. A method of treating hyperlipidemia by administering a therapeutically effective amount of a compound as defined in claim 1.

28. A method of treating hyperlipidemia by administering a therapeutically effective amount of a compound as defined in claim 2.

29. A method of treating hyperlipidemia by administering a therapeutically effective amount of a compound as defined in claim 3.

30. A method of treating hyperlipidemia by administering a therapeutically effective amount of a compound as defined in claim 4.

31. A method of treating hyperlipidemia by administering a therapeutically effective amount of a compound as defined in claim 5.

32. A method of treating hyperlipidemia by administering a therapeutically effective amount of a compound as defined in claim 6.

33. A method of treating hyperlipidemia by administering a therapeutically effective amount of a compound as defined in claim 7.

34. A method of treating hyperlipidemia by administering a therapeutically effective amount of a compound as defined in claim 8.

35. A method of treating hyperlipidemia by administering a therapeutically effective amount of a compound as defined in claim 9.

36. A method of treating hyperlipidemia by administering a therapeutically effective amount of a compound as defined in claim 10.

37. A method of treating hyperlipidemia by administering a therapeutically effective amount of a compound as defined in claim 11.

38. A method of treating hyperlipidemia by administering a therapeutically effective amount of a compound as defined in claim 12.

39. A method of treating hyperlipidemia by administering a therapeutically effective amount of a compound as defined in claim 13.

* * * * *